US012629074B2

(12) United States Patent
Currano et al.

(10) Patent No.: US 12,629,074 B2
(45) Date of Patent: May 19, 2026

(54) WEARABLE MUSCLE ACTIVITY SENSOR AND ELECTRODE

(71) Applicant: The Johns Hopkins University, Baltimore, MD (US)

(72) Inventors: Luke J. Currano, Columbia, MD (US); Korine A. Ohiri, Laurel, MD (US); Leslie H. Hamilton, Silver Spring, MD (US); Matthew T. McGuire, Laurel, MD (US); Paul J. Biermann, Columbia, MD (US); Leah M. Strohsnitter, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1445 days.

(21) Appl. No.: 17/093,799

(22) Filed: Nov. 10, 2020

(65) Prior Publication Data

US 2021/0219895 A1     Jul. 22, 2021

Related U.S. Application Data

(60) Provisional application No. 62/961,737, filed on Jan. 16, 2020.

(51) Int. Cl.
| | |
|---|---|
| *A61B 5/24* | (2021.01) |
| *A61B 5/00* | (2006.01) |
| *A61B 5/256* | (2021.01) |
| *A61B 5/271* | (2021.01) |
| *A61B 5/296* | (2021.01) |
| *A61B 5/313* | (2021.01) |
| *A61B 5/389* | (2021.01) |

(52) U.S. Cl.
CPC .............. *A61B 5/256* (2021.01); *A61B 5/271* (2021.01); *A61B 5/296* (2021.01); *A61B 5/313* (2021.01);

(Continued)

(58) Field of Classification Search
CPC ......... A61B 5/282; A61B 5/25; A61B 5/0006; A61B 5/6804; A61B 5/0245;

(Continued)

(56) References Cited

U.S. PATENT DOCUMENTS

| | | | |
|---|---|---|---|
| 10,973,413 | B2 | 4/2021 | Rapp et al. |
| 11,216,071 | B2 | 1/2022 | Johannes et al. |

(Continued)

OTHER PUBLICATIONS

Takashi Isezaki et al., "Sock-Type Wearable Sensor for Estimating Lower Leg Muscle Activity Using Distal EMG Signals," Sensors 2019, 19, 1954, doi:10.3390/s19081954, pp. 1-18.

*Primary Examiner* — Joseph A Stoklosa
*Assistant Examiner* — Brian M Antiskay
(74) *Attorney, Agent, or Firm* — Noah J. Hayward

(57) ABSTRACT

A muscle activity sensor includes a base textile, an electrode, and an interconnect. The base textile is configured to apply a compression force against a dermal surface of the user. The electrode is coupled to the base textile and includes a sensor layer including a conductive textile coupled to a dermal side of the base textile. The sensor layer is configured to receive electrical signals associated with muscle activity of the user. The electrode may also be configured to provide the electrical signals as an output signal. The interconnect may be coupled to the base textile over a distance from the electrode to an interconnect junction contact such that the interconnect moves with the base textile as the user moves. The interconnect may be further configured to deliver the output signal from the electrode to the interconnect junction contact.

12 Claims, 9 Drawing Sheets

(52) U.S. Cl.
CPC ............ *A61B 5/389* (2021.01); *A61B 5/6804*
(2013.01); *A61B 5/6843* (2013.01); *A61B 2562/0209* (2013.01); *A61B 2562/04* (2013.01)

(58) Field of Classification Search
CPC ... A61B 5/6831; A61B 5/318; A61B 5/02438; A61B 5/259; A61B 5/6805; A61B 5/28; A61B 5/296; A61B 5/6833; A61B 5/389; A61B 5/24; A61B 5/01; A61B 2560/0412; A61B 5/053; A61B 5/6823; A61B 5/681; A61B 5/332; A61B 5/1118; A61B 5/6814; A61B 5/308
USPC .......................... 600/372, 382–393, 508–509
See application file for complete search history.

(56) References Cited

U.S. PATENT DOCUMENTS

| | | | |
|---|---|---|---|
| 11,227,988 B1 | 1/2022 | Venkatasubramanian et al. | |
| 11,272,881 B2 | 3/2022 | Susteric et al. | |
| 2003/0105403 A1* | 6/2003 | Istvan .................. | A61B 5/0006 |
| | | | 600/509 |
| 2006/0211934 A1* | 9/2006 | Hassonjee .............. | D02G 3/441 |
| | | | 600/372 |
| 2007/0038057 A1* | 2/2007 | Nam ..................... | A61B 5/6805 |
| | | | 600/388 |
| 2009/0227856 A1* | 9/2009 | Russell ................ | A61B 5/6805 |
| | | | 600/388 |
| 2010/0185076 A1* | 7/2010 | Jeong ................... | A61B 5/6805 |
| | | | 600/388 |
| 2014/0135608 A1* | 5/2014 | Gazzoni ................. | A61B 5/256 |
| | | | 427/2.12 |
| 2015/0040282 A1* | 2/2015 | Longinotti-Buitoni ..................... | |
| | | | A61B 5/7405 |
| | | | 2/69 |
| 2015/0094559 A1* | 4/2015 | Russell ................. | A61B 5/274 |
| | | | 600/386 |
| 2016/0278658 A1* | 9/2016 | Bardy ................. | A61B 5/6833 |
| 2017/0196513 A1 | 7/2017 | Longinotti-Buitoni et al. | |
| 2017/0224280 A1* | 8/2017 | Bozkurt ................ | G01L 5/0014 |
| 2017/0340226 A1* | 11/2017 | Takagahara ............. | A61B 5/28 |
| 2017/0354372 A1* | 12/2017 | Varadan ................. | A61B 5/282 |
| 2018/0042509 A1* | 2/2018 | Wernke ................ | A61B 5/6825 |
| 2018/0310855 A1* | 11/2018 | Connor ................ | A61B 5/6814 |

\* cited by examiner

WEARABLE MUSCLE ACTIVITY SENSOR AND ELECTRODE

CROSS-REFERENCE TO RELATED APPLICATIONS

This application claims priority to and the benefit of prior-filed, U.S. Provisional Application Ser. No. 62/961, 737 filed on Jan. 16, 2020, the entire contents of which are hereby incorporated herein by reference.

STATEMENT OF GOVERNMENTAL INTEREST

This invention was made with Government support under contract number N4175618C3022 awarded by the Navy Engineering Logistics Office (NELO). The Government has certain rights in the invention.

TECHNICAL FIELD

Example embodiments generally relate to wearable sensors and, in particular, relate to wearable muscle activity sensors for detecting electrical signals associated with muscle activity.

BACKGROUND

The detection of muscle activity has proven useful in a number of contexts, particularly in the areas of exercise science and also to detect neuromuscular abnormalities. One manner of detecting muscle activity is to detect electrical signals that travel from the brain via the nervous system to control the muscle, also known as electromyography. These signals can be detected by a sensor that, in some instances, is inserted through the skin and into the muscle as a pin that is connected to a wire. Such an approach is obviously invasive and can be uncomfortable for the individual. Also, the insertion of a sensor into the muscle itself may not be practical in many contexts, particularly when tracking signals and associated movements during non-medical, standard exercise scenarios. An alternative is surface electromyography, typically performed with electrodes topped with conductive gel and adhered to the skin with an adhesive. These are inconvenient and uncomfortable, especially over areas of the skin with hair, and the gel dries out over time. As such, an improved, more convenient sensor that avoids invasive approaches and is still reliable for detecting muscle activity is needed.

BRIEF SUMMARY OF SOME EXAMPLES

According to some example embodiments, a muscle activity electrode is provided. The muscle activity electrode may comprise a base textile, a sensor layer, an interconnect contact, and a feedthrough element. The base textile may be configured to apply a compression force against a dermal surface of a user. In this regard, the base textile may have a dermal side and an external side. The sensor layer may be coupled to the base textile and may comprise a conductive textile. The sensor layer may be configured to receive electrical signals associated with muscle activity of the user. The interconnect contact may be coupled to the base textile. A feedthrough element may be configured to form an electrical connection between the sensor layer and the interconnect contact to deliver the electrical signals from the sensor layer to the interconnect contact to be provided as an output signal.

According to some example embodiments, a muscle activity sensor is provided. The muscle activity sensor may comprise a base textile, an electrode, and an interconnect. The base textile may be configured to apply a compression force against a dermal surface of a user. In this regard, the base textile may have a dermal side and an external side. The electrode may be coupled to the base textile and may comprise a sensor layer comprising a conductive textile coupled to the dermal side of the base textile. The sensor layer may be configured to receive electrical signals associated with muscle activity of the user and the electrode may be configured to provide the electrical signals as an output signal. The interconnect may be coupled to the base textile over a distance from the electrode to an interconnect junction contact such that the interconnect moves with the base textile as the user moves. The interconnect may be configured to deliver the output signal from the electrode to the interconnect junction contact.

According to some example embodiments, another muscle activity sensor is provided. The muscle activity sensor may comprise a base textile, an electrode, an interconnect, and a tab assembly. The base textile may be configured to apply a compression force against a dermal surface of the user. The base textile may have a dermal side and an external side. The electrode may be coupled to the base textile and configured to receive electrical signals associated with muscle activity of the user and output the electrical signals as an output signal. The interconnect may be coupled to the base textile over a distance from the electrode to an interconnect junction contact such that the interconnect moves with the base textile as the user moves. The interconnect may be configured to deliver the output signal from the electrode to the interconnect junction contact. The tab assembly may be configured to electrically connect the junction to a circuit board socket. The tab assembly may comprise a conductive element affixed to a support layer, where the conductive element may be electrically connected to the interconnect junction contact. The support layer and the conductive element may form an extension portion that extends over the base textile with a gap between the conductive element and the base textile such that the conductive element and the support layer form a plug configured to engage with the circuit board socket.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

DETAILED DESCRIPTION

Figure 1:
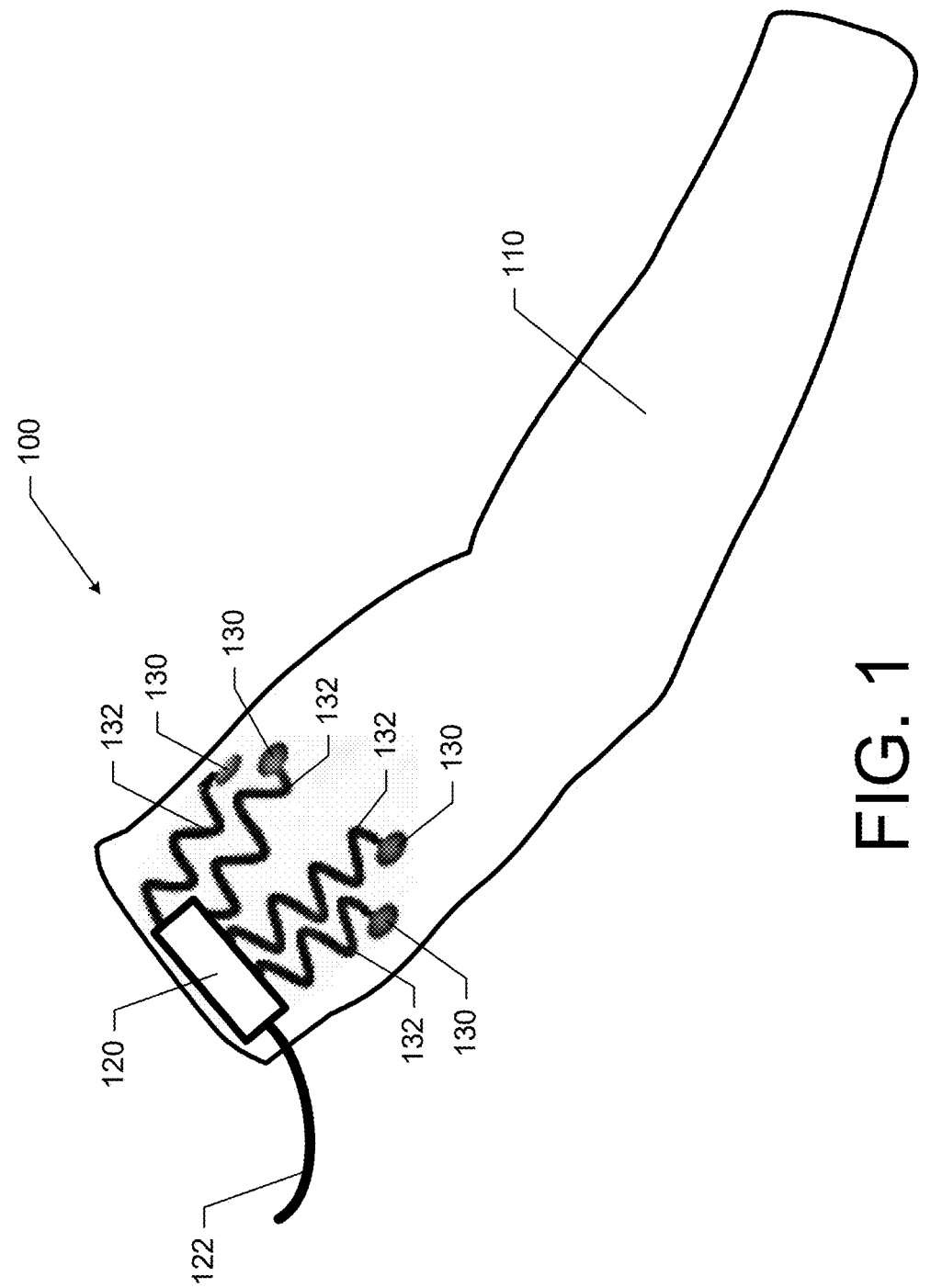
FIG. 1 illustrates an example muscle activity sensor according to some example embodiments.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. As used herein, coupling should be understood to relate to direct or indirect connection that, in either case, enables functional interconnection of components that are coupled to each other.

According to some example embodiments, wearable muscle activity electrodes, sensors, and associated methods, are described herein. The muscle activity sensors and associated electrodes may, according to some example embodiments, be used to collect electromyography (EMG) signals that may be used to assess muscle health and the nerves that control the muscles. Such sensors may be a type of physiological sensor. In this regard, a muscle activity sensor, which may comprise one or more muscle activity electrodes, may be integrated into a base textile such as sleeve, shirt, pants, or other type of garment. According to some example embodiments, the base textile may be formed of a textile with elastic properties to provide a compression force against the skin or dermal surface of the user wearing the base textile. A muscle activity electrode that is coupled to the base textile may be pressed against the dermal surface at a location adjacent to a muscle. The electrode may comprise a sensor layer that is formed of, for example, a conductive textile, and may be configured to receive electrical signals originating from and associated with muscle activity of the user. Further, the electrode may be configured to deliver the electrical signals detected in the muscle to an interconnect that is also coupled to the base textile. The interconnect may operate to deliver the electrical signals from the electrode to, for example, a junction that is configured for coupling to a processing device. The interconnect may therefore extend across a length on the base textile and may therefore be configured to move with the base textile when, for example, a user moves (e.g., bends at a joint). To reduce the mechanical forces applied to the interconnect (e.g., due to stresses and strains on the base textile and accordingly the interconnect due to movement of the user) the interconnect may also be formed of a conductive textile and may be shaped in a serpentine pattern, which may limit the stresses and strains on the interconnect, but also minimize the variation in electrical resistance of the interconnect as a result of shape changes from user movement. According to some example embodiments, the interconnect may be affixed to the exterior surface of the base textile and travel along the exterior surface of the base textile in a serpentine pattern to a junction. Further, according to some example embodiments, a number of interconnects may terminate at the junction area, with each interconnect having a respective interconnect junction contact. According to some example embodiments, two interconnects may be formed as a nested serpentine pair or as twisted pair as further described herein. To provide for connectivity between the interconnect junction contacts and a circuit board, a tab assembly may be may be affixed to the interconnect junction contacts. The tab assembly may include a conductive element affixed to a support layer (e.g., formed of a polyimide film) that form a plug. The plug of the tab assembly may be received into a circuit board socket to form electrical connections to each of the interconnect junction contacts.

While some example embodiments describe herein are directed to applications involving muscle activity sensing, it is contemplated that example embodiments may be implemented to detect other electrical signals emanating from the body. For example, some example embodiments may be employed in the context of electrophysiological sensing, such as EEG (electroencephalogram) sensing of the brain, ECG/EKG (electrocardiogram/elektrokardiogramm) sensing of the heart, bioimpedance of the body or parts of the body, or galvanic skin response (GSR). Such example embodiments may differ, for example, in the placement of the electrodes relative to the sensing target (e.g., brain, heart, etc.).

Having described some example embodiments in general terms, FIG. 1 illustrates an example muscle activity sensor 100. As mentioned above, the muscle activity sensor 100 may be constructed on a base textile 110. Although the base textile 110 may take any form of clothing that may be worn or applied to a user's body (e.g., shirt, shorts, pants, calf sleeve or band, arm sleeve or band, or the like), the base textile 110 of FIG. 1 is shown as an arm sleeve. According to some example embodiments, the base textile 110 may include a cuff that, for example, may be secured in place using Velcro® or other hook and loop fasteners. According to some example embodiments, the base textile 110 may have an elastic property and may therefore be configured to apply a compression force against the skin or dermal surface of the user. As such, the base textile 110 may have a dermal side and an external side, with the external side being shown in FIG. 1. The base textile 110 may formed of or comprise spandex, elastane, Lycra®, or another textile comprising, for example, polyether-polyurea copolymer fibers.

The muscle activity sensor 100 may also include muscle activity electrodes 130. An electrode 130 may be constructed such that the base textile 110 supports and forms a component of the electrode 130. The electrode 130 may be configured to detect and receive electrical signals, emitted by a muscle during a muscle movement, for delivery to, and analysis by, processing circuitry. The electrode 130 may be coupled to the base textile 110 in variety of ways to place the electrode 130 in close proximity to or adjacent to a target muscle. For example, the electrode 130 may be coupled to the base textile 110 by being sewn or embroidered onto the base textile 110. Alternatively, the electrode 130 may be affixed to the base textile 110 via an adhesive (e.g., hot-melt adhesive), via lamination (e.g., heat lamination), or the like. According to some example embodiments, the electrode 130 may have a component that is disposed on the internal, dermal side of the base textile 110 such that the component may be in direct contact with the skin or dermal surface of the user. Further, the electrodes 130 may be located, based on the type of garment formed by the base textile, in a position in close proximity to or adjacent to a target muscle of the user. As shown in FIG. 1, the electrodes 130 are located proximate or adjacent to the bicep and tricep muscles. According to some example embodiments, to monitor a given muscle, two electrodes 130 may be used and the signal differential between the electrical signals received by the respective electrodes 130 may be used for muscle response monitoring, electromyography applications, or the like.

The electrodes 130 may deliver the received electrical signals from the muscles to an interconnect 132. An interconnect 132 may also be coupled to the base textile 110, and may be configured to the deliver the electrical signal received by a respective electrode 130 to, for example, a junction area. For coupling, similar to the electrode 130, the interconnect 132 may be coupled to the base textile 110 by being sewn to, or embroidered on, the base textile 110. Alternatively, the interconnect 132 may be affixed to the base textile 110 via an adhesive (e.g., hot-melt adhesive), via lamination (e.g., heat lamination), or the like. Further, the interconnect 132 may also be reinforced and/or electrically insulated by performing a potting operation on the interconnect 132 by curing, for example, a urethane layer (e.g., at room temperature) or heat laminating a urethane layer to the interconnect 132. The interconnect 132 may be coupled to either the dermal side or the exterior side of the base textile 110. As such, the interconnect 132 may be the component that transmits the output signal of the electrode 130 from a position proximate to or adjacent to a muscle to a junction area for provision to processing circuitry. According to some example embodiments, the interconnect 132 may be formed of a conductive textile to support conduction of the electrical signals. For example, the interconnect 132, as a conductive textile, may be formed of, for example, synthetic elastane fibers with a conductive coating or synthetic elastane fibers woven with conductive fibers. According to some example embodiments, a spandex, Lycra®, or the like coated with metal (e.g., silver) may be used for the interconnect 132. Accordingly, the shape of the interconnect 132 may be formed via laser cutting or die or stamp cutting of the conductive textile. According to some example embodiments, the interconnect 132 may be formed by other materials such as, for example, conductive paints or inks applied to the base textile 110.

Additionally, to limit the stresses and strains placed on an interconnect 132, the interconnect 132 may be formed in a variety of shapes. For example, the interconnect 132 may take a non-linear shape. In this regard, a portion of the interconnect 132 may take a serpentine shape, which may include a sinusoidal shape, a zig-zag shape, or the like. Such shapes may be configured to reduce the stress and strain on the interconnect 132, which may affect the electrical resistance across the interconnect 132. Because, for example, a serpentine shape is not subjected to high stresses or strains when the base textile 110 is moved (e.g., stretched by movement of the user), the electrical resistance across the interconnect 132 may be remain within a threshold range (e.g., below 1 kOhm) and thus relatively constant during movement of the user's body. As such, electrical signal measurements from the muscle can be reliable, even when the user is moving.

The interconnects 132 may terminate at a junction area where connections may be made to a tab assembly as further described below. The tab assembly may form or include a plug that may be received into a circuit board socket of a circuit board 120. As such, the circuit board 120 may be electrically connected to the interconnects 132 via the tab assembly and the circuit board socket. The circuit board 120 may include processing circuitry for analyzing the output signals provided by the electrodes 130. In this regard, the circuit board 120 may include a processor and a memory configured to perform an analysis of the electrical signals received from the target muscles. Additionally, the circuit board 120 may include a communications interface that may be configured to transmit representations of the electrical signals received from the target muscles via a wired connection 122 or a wireless connection via an antenna.

Figure 2:
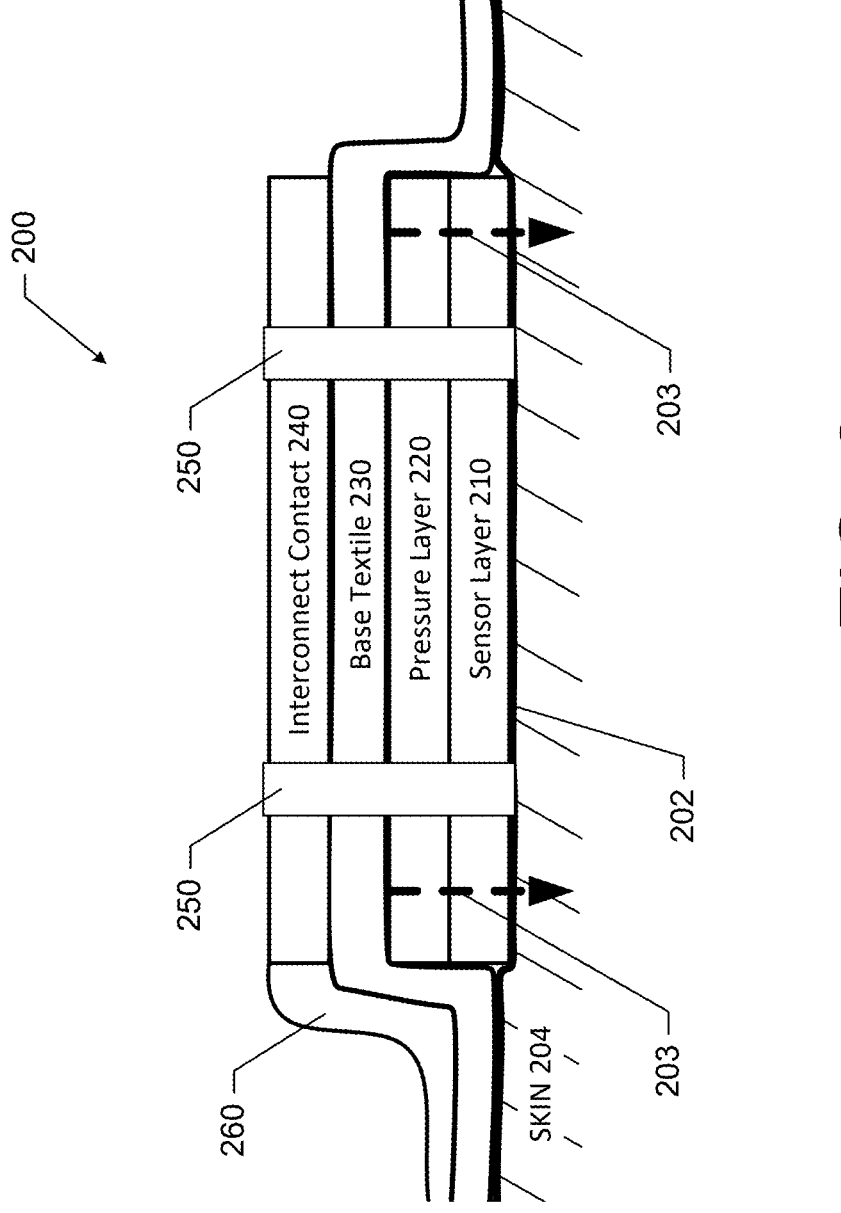
FIG. 2 illustrates a cross-section view of a muscle activity electrode according to some example embodiments.

Now referring to FIG. 2, a cross-section view of a muscle activity electrode 200, according to some example embodiments, is shown. The electrode 200 may be the same or similar to the electrode 130 in operation and structure. In this regard, the electrode 200 may comprise a sensor layer 210, a pressure layer 220, a base textile 230, an interconnect contact 240, and a feedthrough element 250. The electrode 200 may be positioned to be in direct contact to the skin 204 of the user and, more specifically, the dermal surface 202 of the skin 204 of the user. As described above, the base textile 230, which may be the same or similar to the base textile 110 in function and structure, may serve as a substrate for the electrode 200 and may also operate to apply a compression force (as indicated by the arrows 203) to press the electrode 200 against the dermal surface 202.

The sensor layer 210 may be configured to be in contact with the dermal surface 202 to receive electrical signals associated with an underlying muscle. Further, the sensor layer 210 may be formed of a conductive textile. In this regard, the sensor layer 210 may be formed of, for example, a conductive textile comprising synthetic elastane fibers with a conductive coating or synthetic elastane fibers woven with conductive fibers. According to some example embodiments, a silver (metal) spandex, Lycra®, elastane, or the like may be used for the sensor layer 210. Further according to some example embodiments, the sensor layer 210 may be formed of other types of conductive textiles, such as, polyester or another textile coated with poly(3,4-ethylenedioxythiophene) polystyrene sulfonate (PEDOT:PSS). According to some example embodiments, combinations of, for example, conductive textiles may be used, such as combining silver Lycra® with PEDOT:PSS-coated polyester in layers to form the sensor layer 210. Alternatively, according to some example embodiments, the sensor layer 210 may be formed by other materials such as, for example, conductive paints or inks. As a conductive textile, the sensor layer 210 may be configured to absorb, hold, or wick moisture to improve the electrical contact (e.g., reduce electrical resistance) between the sensor layer 210 and the dermal surface 202. In this manner, the inclusion of moisture (e.g., water, sweat, etc.) to the sensor layer 210 may increase the electrode 200's ability to reliably detect the electrical signals associated with the target muscle.

In some example embodiments, the sensor layer 210 may be applied to the base textile 230. However, according to some example embodiments, a pressure layer 220 may be disposed between the sensor layer 210 and the base textile 230. The pressure layer 220 may be configured to add thickness between the dermal layer contacting surface of the sensor layer 210 and the base textile 230. By doing so, the compression force generated by the base textile 230 on the dermal surface 202 may be increased to ensure reliable contact between the sensor layer 210 and the dermal surface 202. According to some example embodiments, the pressure layer 220 may be formed or comprise a foam material.

With the pressure layer 220 and the sensor layer 210 being disposed on the dermal side of the base textile 230, the electrode 200 may also include an interconnect contact 240 disposed on the external side of the base textile 230. The interconnect contact 240 may be a portion of or a connection point to an interconnect 260, which may be the same or similar to the interconnect 132 in function and structure. As such, the interconnect contact 240 may be formed of the same or similar materials as the interconnect 132, and therefore, according to some example embodiments, the interconnect contact 240 may be formed of a conductive textile or a conductive paint or ink.

To electrically connect the interconnect contact 240 to the sensor layer 210, the electrode 200 may include a feed-through element 250. The feedthrough element 250 may be formed of a conductive material (e.g., metal) that pierces through the interconnect contact 240 and the base textile 230 to come into physical and electrical contact with the sensor layer 210. According to some example embodiments, in addition to forming an electrical connection between the interconnect contact 240 and the sensor layer 210, the feedthrough element 250 may mechanically couple the sensor layer 210, the pressure layer 220, and the interconnect contact 240 to the base textile 230. According to some example embodiments, the feedthrough element 250 may be a metallic snap or grommet. Alternatively, according to some example embodiments, the feedthrough element 250 may be formed by a conductive thread or yarn.

Figures 3A, 3B, 3C:
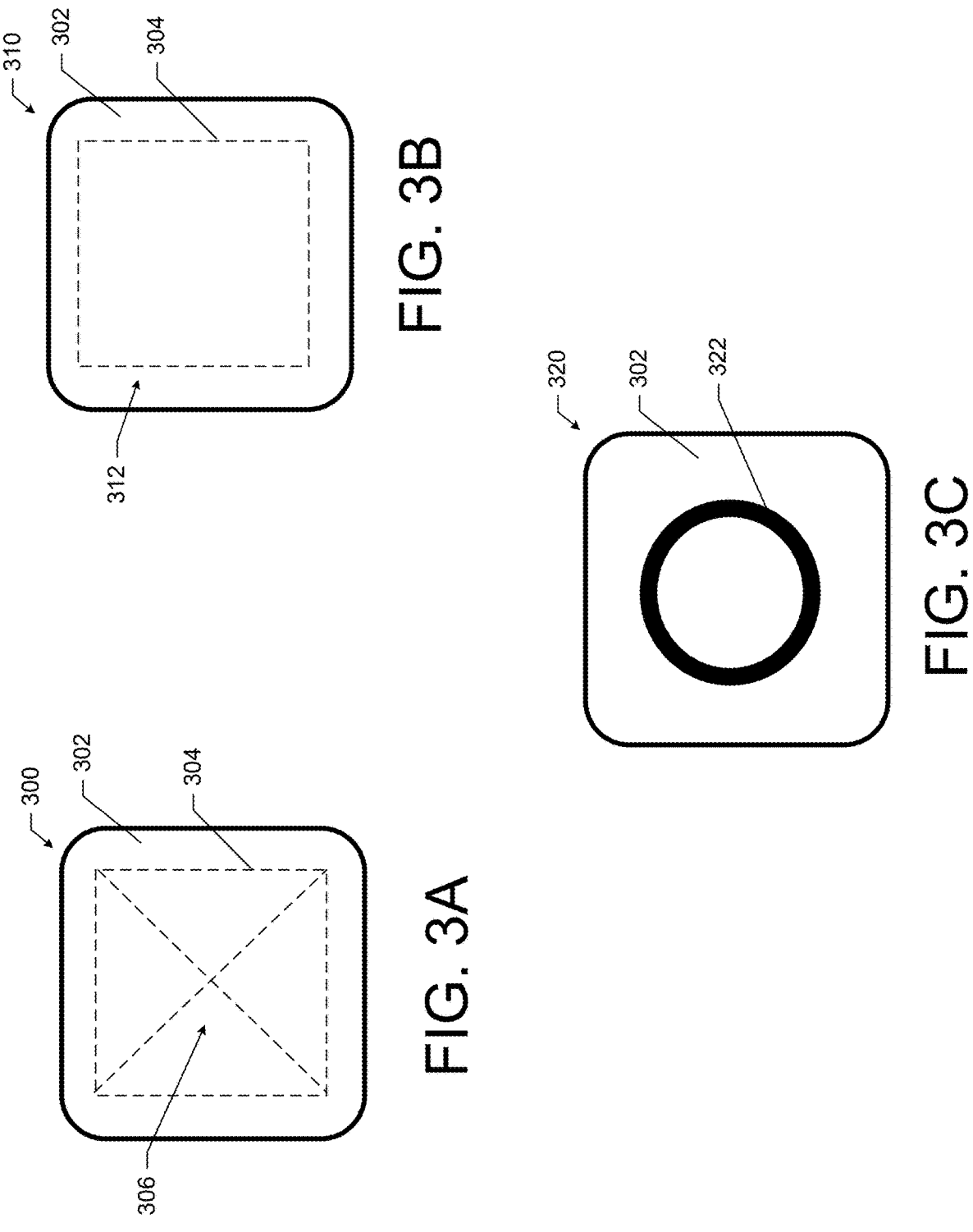
FIGS. 3A to 3C illustrate top views of a muscle activity electrodes with different options for feedthroughs according to some example embodiments.

FIGS. 3A to 3C illustrate top views of a few example muscle activity electrodes with different options for feedthroughs according to some example embodiments. In this regard, FIG. 3A illustrates an example electrode 300 comprising a interconnect contact 302 and a feedthrough element 306. The feedthrough element 306 may be formed by, for example, a conductive thread sewn into the electrode 300. The conductive thread may be sewn around the edges of the generally square interconnect contact 302 and in an x-pattern through the center of the electrode 300 to form the feedthrough element 306.

FIG. 3B illustrates an example electrode 310 comprising a interconnect contact 302 and a feedthrough element 312. The feedthrough element 312 may be formed by conductive thread sewn into the electrode 310. The conductive thread may be sewn around the edges of the generally square interconnect contact 302 to form the feedthrough element 306. While the interconnect contact 302 is shown as being generally square, the contact may take a variety of different shapes (e.g., circle, oval, rectangle, triangle, ring or donut, bow-tie, or the like). Further, regardless of the shape of the interconnect connect 302 (and accordingly, the shape of the electrode) the conductive thread may be sewn, for example, around the edges of the interconnect connect 302.

Finally, FIG. 3C illustrates an example electrode 320 comprising a interconnect contact 302 and a feedthrough element 322. The feedthrough element 322 may be formed by a conductive snap device or a grommet device that has components that are forced into the electrode 310 and secured together. The snap or grommet may be pressed into the electrode 320 and the interconnect contact 302 to form the feedthrough element 322.

Figure 4:
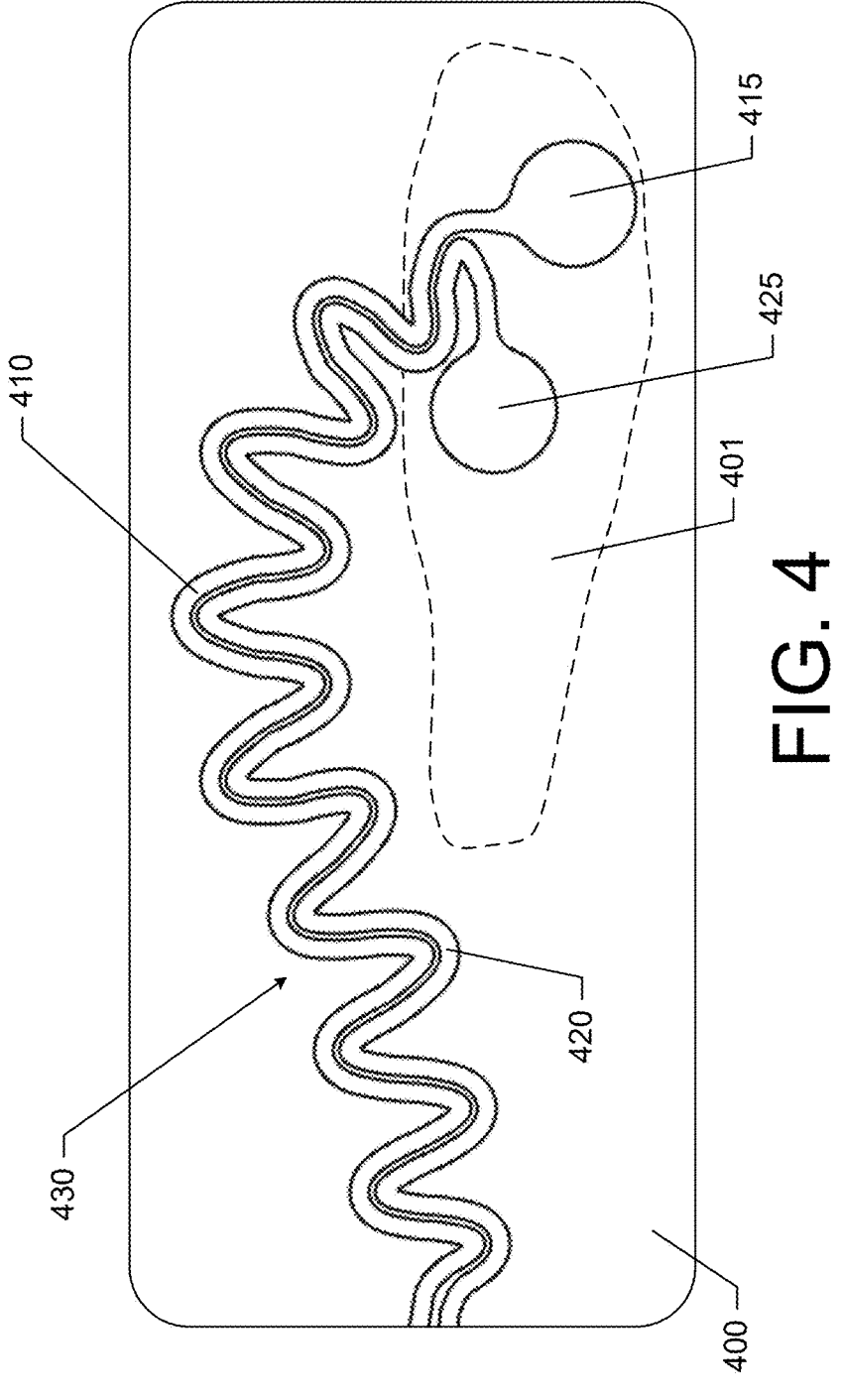
FIG. 4 illustrates a pair of nested serpentine interconnects according to some example embodiments.

FIG. 4 illustrates a sensor arrangement that comprises a pair 430 of nested serpentine interconnects 410 and 420 connected to respective electrodes 415 and 425 affixed to a base textile 400 proximate to a target muscle 401 according to some example embodiments. As shown, the interconnects 410 and 420 follow similar paths from the electrodes 415 and 425. Further, the pair 430 are configured to move together due to their close proximity and therefore any effect of stress and strain on the electrical resistance of the electrodes 415 and 425 may be same or similar. Each interconnect 410 and 420 may include segments or portions that are sinusoidal in structure. However, some bending and curvatures may be introduced to the sinusoidal structures. As a serpentine structure, the interconnects 410 and 420 may include a portion with a sinusoidal structure, but may, in some example embodiments, also include a components that introduce bends and turns for positioning the interconnects 410 and 420 between the target muscle 401 and the junction area (not shown). Additionally, the portion of the pair 430 that is structured as a nested sinusoid or components of a nested sinusoid include segments where one of the interconnects is subjected to a tighter turn (on an interior of the turn) and the other of the interconnects is subjected to wider turn (on the exterior of the turn). As the nested sinusoidal shape travels across the base textile 420, the interconnect that is subjected to a tighter turn is subsequently subjected to a wider turn and vice versa. Because of this relationship within the pair 430, the lengths of the interconnects may be the same or similar and may be subjected to the same or similar strain and stress forces when the base textile 400 moves or stretches.

Additionally, because the pair 430 maintain adjacency across a substantial portion of their lengths, an inductive coupling may occur between interconnects 410 and 420. Such inductive coupling can operate to reduce noise by canceling some effects of noise that may introduced to the electrical signals being delivered by the interconnects 410 and 420.

Figures 5A, 5B:
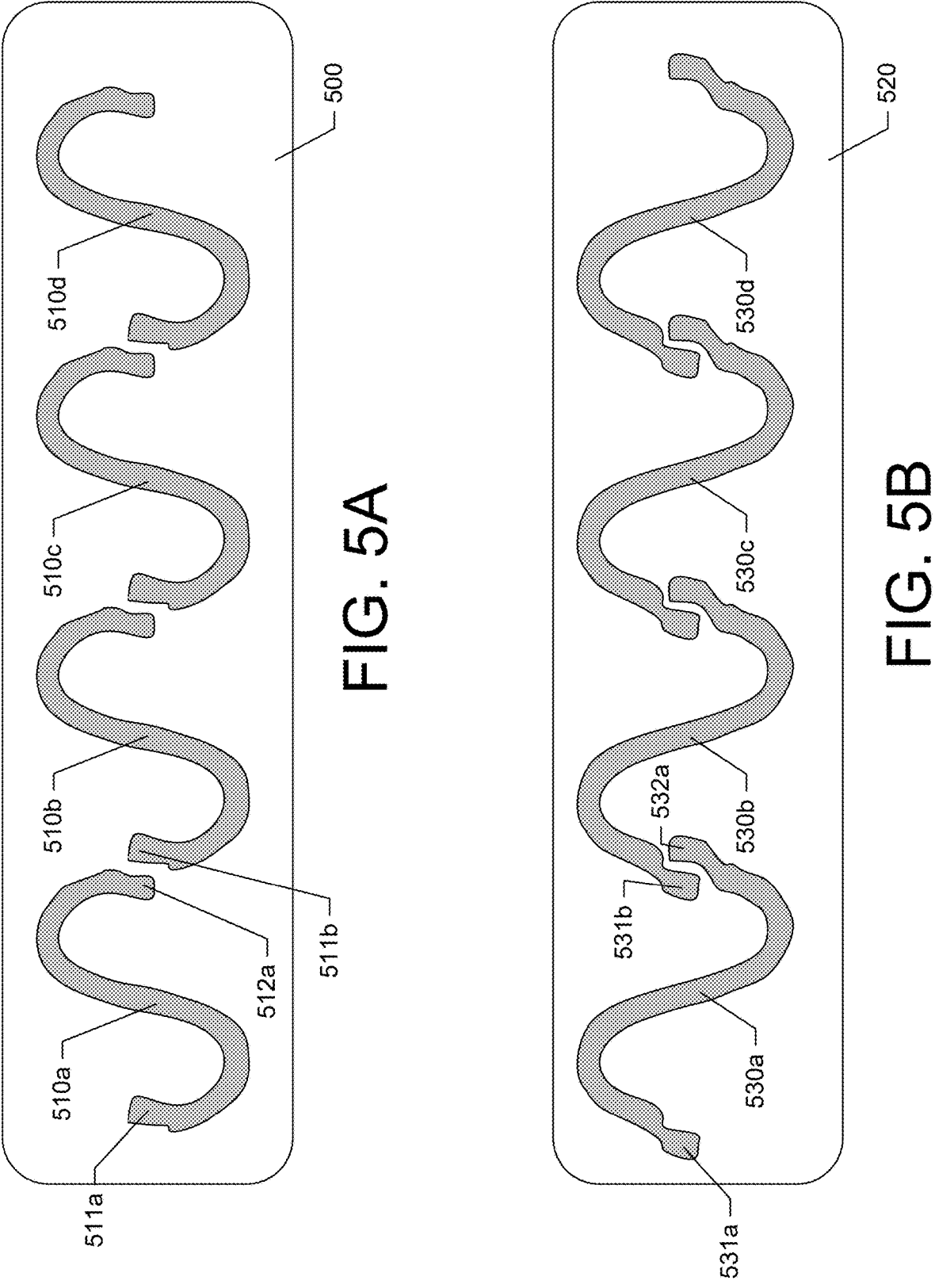
FIGS. 5A and 5B illustrate components of a twisted pair interconnect according to some example embodiments.
Figure 5C:
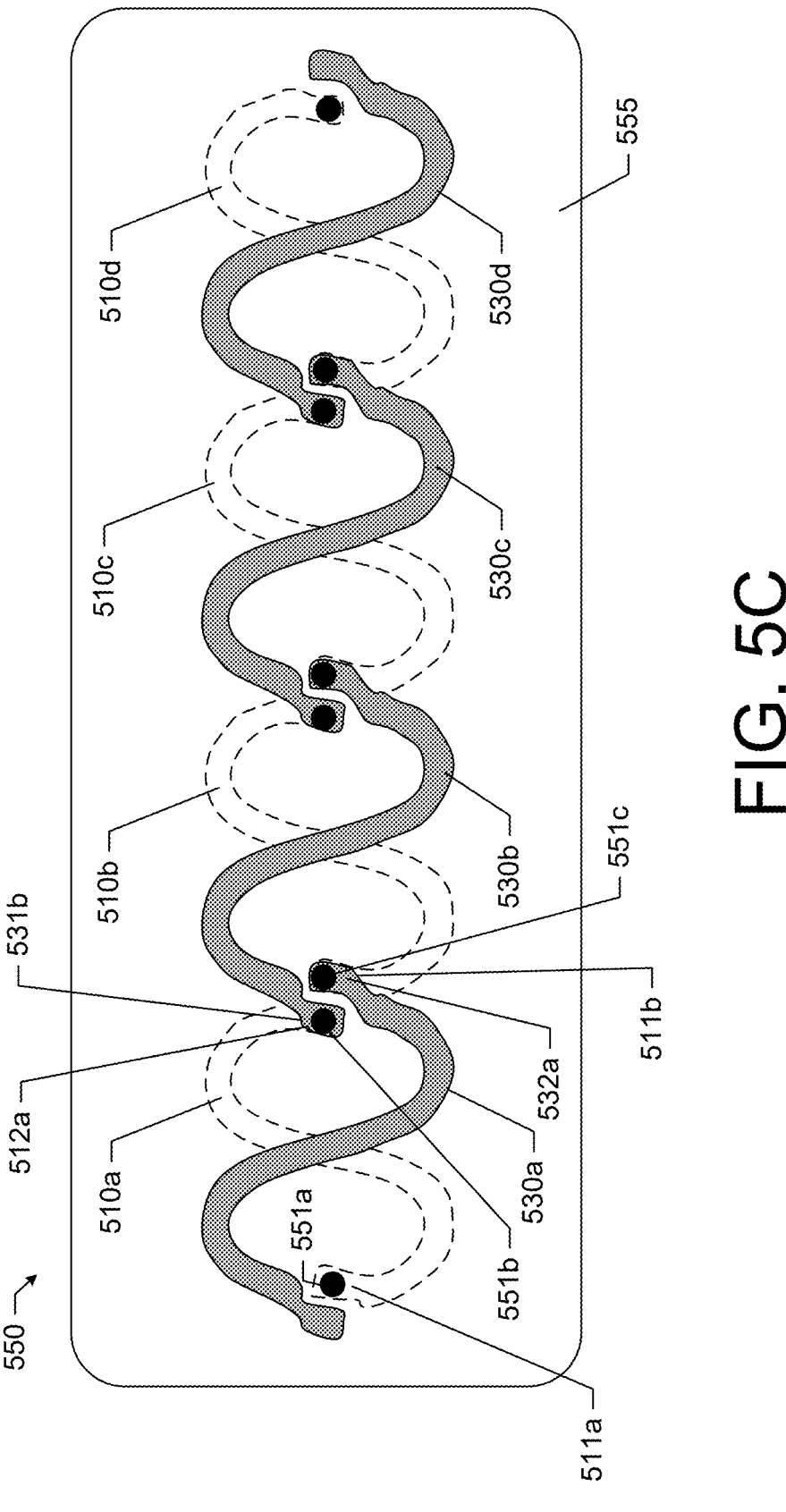
FIG. 5C illustrates an assembled twisted pair interconnect according to some example embodiments.

In some instances, to increase the inductive coupling that may occur between two interconnects to reduce noise, a twisted pair configuration for the interconnects may be employed as described with respect to FIGS. 5A to 5C. In this regard, conductive segments of piecewise sinusoids (e.g., formed using the conductive textiles described herein) may formed on a substrate. With reference to FIG. 5A, a first substrate 500 may support repeating piecewise sinusoidal segments 510a, 510b, 510c, and 510d. Individually, each piecewise sinusoidal segments 510a, 510b, 510c, and 510d may take the form of a single period of a sinusoid and, again, the sinusoidal shape may be used to reduce the stress and strain on the segments when applied to a movable base textile. With reference to piecewise sinusoidal segments 510a as an example, a piecewise sinusoidal segment 510a may comprise a first end contact 511a disposed at one end of the piecewise sinusoidal segment 510a, and a second end contact 512a disposed at the other end of the piecewise sinusoidal segment 510a. As further described below the piecewise sinusoidal segments 510a, 510b, 510c, and 510d may form one side layer of a twisted pair of interconnects.

Similarly, as shown is FIG. 5B, a second substrate 520 may support repeating piecewise sinusoidal segments 530a, 530b, 530c, and 530d. Individually, each piecewise sinusoidal segments 530a, 530b, 530c, and 530d may take the form of a single period of a sinusoid and, again, the sinusoidal shape may be used to reduce the stress and strain on the segments when applied to a movable base textile. With reference to piecewise sinusoidal segments 530a as an example, a piecewise sinusoidal segment 530a may comprise a first end contact 531a disposed at one end of the piecewise sinusoidal segment 530a, and a second end contact 532a disposed at the other end of the piecewise sinusoidal segment 530a. As further described below the piecewise sinusoidal segments 530a, 530b, 530c, and 530d may form another side layer of a twisted pair of interconnects. Of note, with the ends of the piecewise sinusoidal segments 510a, 510b, 510c, and 510d aligned with the ends of the piecewise sinusoidal segments 530a, 530b, 530c, and 530d, the segments are formed out-of-phase (e.g., 180 degrees out of phase).

FIG. 5C illustrates an assembled twisted pair interconnect 550 that is constructed with the piecewise sinusoidal segments 510a, 510b, 510c, and 510d and the piecewise sinusoidal segments 530a, 530b, 530c, and 530d, according to some example embodiments. In this regard, an insulating layer 555 (which, in some example embodiments, may be the base textile) may be disposed between the piecewise sinusoidal segments 510a, 510b, 510c, and 510d and the piecewise sinusoidal segments 530a, 530b, 530c, and 530d. According to some example embodiments, the insulating layer 555 may be formed of thermoplastic urethane (TPU). As such, the piecewise sinusoidal segments 510a, 510b, 510c, and 510d may be applied to a first side of the insulating layer 555 (e.g., the top side of the insulating layer 555 as shown in FIG. 5C) and the piecewise sinusoidal segments 530a, 530b, 530c, and 530d may be applied to a second side of the insulating layer 555 (e.g., the bottom side of the insulating layer 555 as shown in FIG. 5C). Application of the segments to the insulating layer 555 may involve removal of the segments from their respective substrates 500 and 520. In this regard, the piecewise sinusoidal segments 510a, 510b, 510c, and 510d may be positioned such that the ends of the segments overlap with the ends of the piecewise sinusoidal segments 530a, 530b, 530c, and 530d as shown in FIG. 5C.

To electrically connect the segments, conductive vias may be included in the twisted pair interconnect 550. In this regard, a via may be same or similar to the feedthroughs described above in both function and structure. In this regard, for example, the via 551a may be positioned on the segment end 511a to permit electrical connection to the segment 510a on the top side of the insulting layer 555. Further, via 551b may be included to form an electrical connection between the segment end 512a of segment 510a and the segment end 531b of the segment 530b. Similarly, the via 551c may be included to form an electrical connection between the segment end 511b of segment 510b and the second end contact 532a of the segment 530a. As shown in FIG. 5C, similar vias may be installed between the segment end to form connectively across the assembly.

The assembled twisted pair interconnect 550 travels between the sides of the insulating layer 555 through the vias. As such, if each conductive path is followed through the twisted pair interconnect 550, the paths change sides of the insulating layer 555 as they move from one end to the other. Further, the paths overlap or crisscross along the length of the twisted pair interconnect 550. As a result of these characteristics, the individual interconnects of the twisted pair interconnect 550 are twisted together to form a twisted pair. As such, inductive coupling between the interconnects is increased thereby realizing noise reduction benefits, while also maintaining a sinusoidal or serpentine pattern to minimize stresses and strains on the individual interconnects due to movement of a base textile that the assembled twisted pair interconnect 550 may be affixed to. According to some example embodiments, other similar arrangements that approximate a twisted pair are also possible, such as, for example, arrangements with half-period or three-quarter-period segments, two-period or another integer-period segments, or combinations thereof, where the conductive path switches sides of the insulating layer 555 at an end of each segment.

Figure 6:
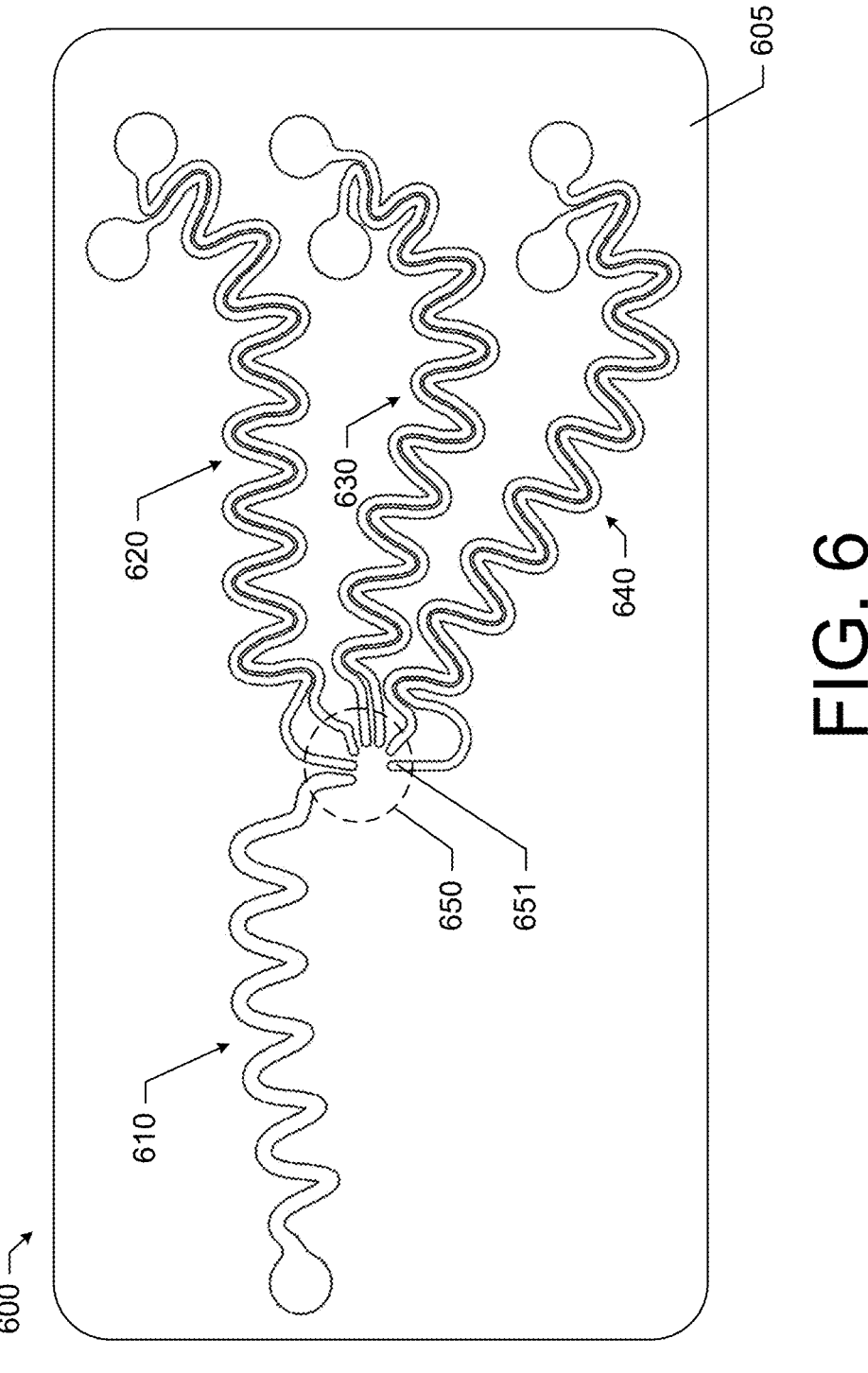
FIG. 6 illustrates a collection of interconnects that extend to a common junction according to some example embodiments.

FIGS. 6, 7, 8A, and 8B will now be described to illustrate an example junction area and a tab assembly for connecting interconnects of a muscle activity sensor to a circuit board (e.g., a hard-to-soft connection), according to some example embodiments. In this regard, FIG. 6 illustrates an interconnect arrangement 600 comprising a base textile 605, an interconnect 610 (which may be used as a ground interconnect, for example, on a user's wrist) and interconnect pairs 620, 630, and 640. As shown, each of the interconnects may terminate at interconnect junction contacts in a junction area 650. For example, an interconnect junction contact may be a terminal end portion of an interconnect that is configured for connection to a tab assembly as described below. One of the interconnects of the interconnect pair 640 terminates at an interconnect junction contact 651 within the junction area 650.

Figure 7:
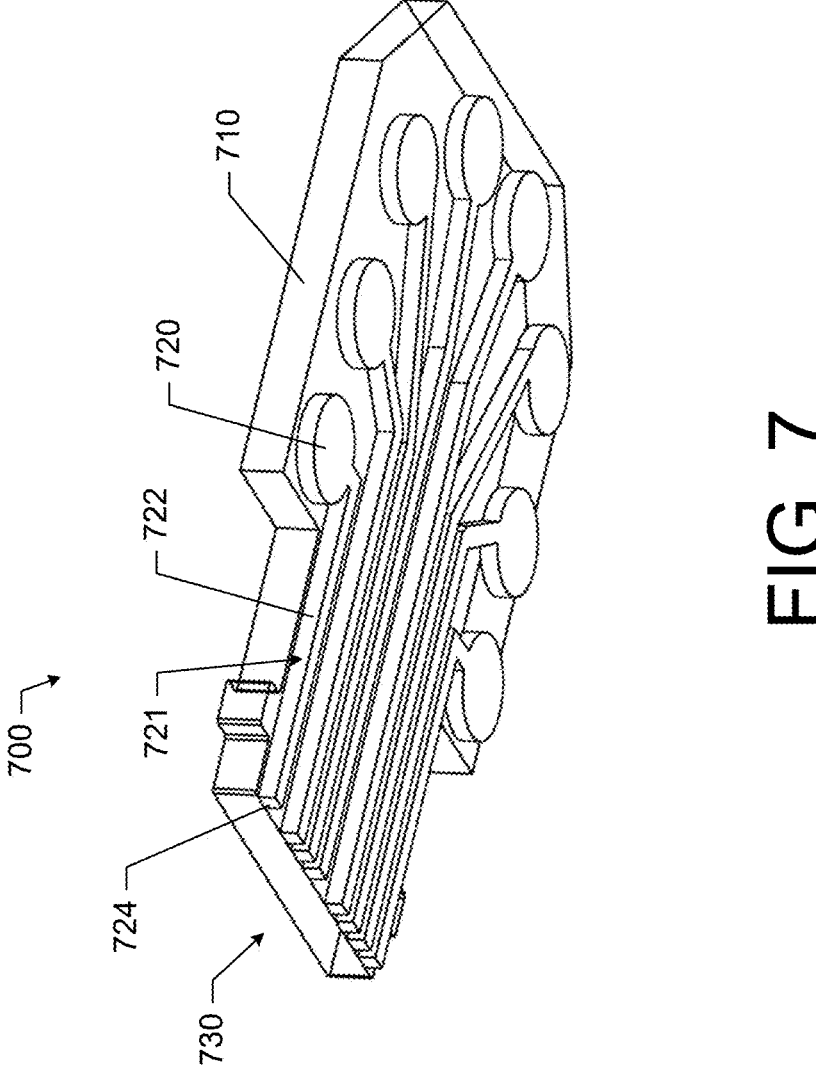
FIG. 7 illustrates a tab assembly according to some example embodiments.

Referring now to FIG. 7, a tab assembly 700 is shown. The tab assembly 700 may comprise a number of conductive elements 721 affixed to a support member 710. Each conductive element 721 may be associated with a respective interconnect of a muscle activity sensor, and may be formed of a conductive material (e.g., a metal, such as, copper, silver, aluminum, etc.). In this regard, each conductive element 721 may comprise a pad 720 configured to form an electrical connection with an interconnect junction contact. Further, the conductive element 721 may comprise a trace 722 and a plug end 724. The trace 722 may be an electrical connector between the pad 720 and the plug end 724. The plug end 724 may be a contact point for the conductive element 721 to electrically connect the conductive element 721 (and thus the associated interconnect) to a socket contact, for example, within a circuit board socket on a circuit board. As such, the plug end 724 may be one of a number of plug ends associated with respective conductive elements, and the plug ends together with an end of the support member 710 may form a plug 730.

The support member 710 may be formed of a flexible material, such as materials that are used in flexible circuit boards. For example, the support member 710 may be formed by or comprise a polyimide film (e.g., KAPTON® film). The support member 710 may have physical properties that permit some bending, but are resilient to strain forces. As such, the conductive elements that are affixed to the support member 710 may be protected by these physical properties of the support member 710.

Figures 8A, 8B:
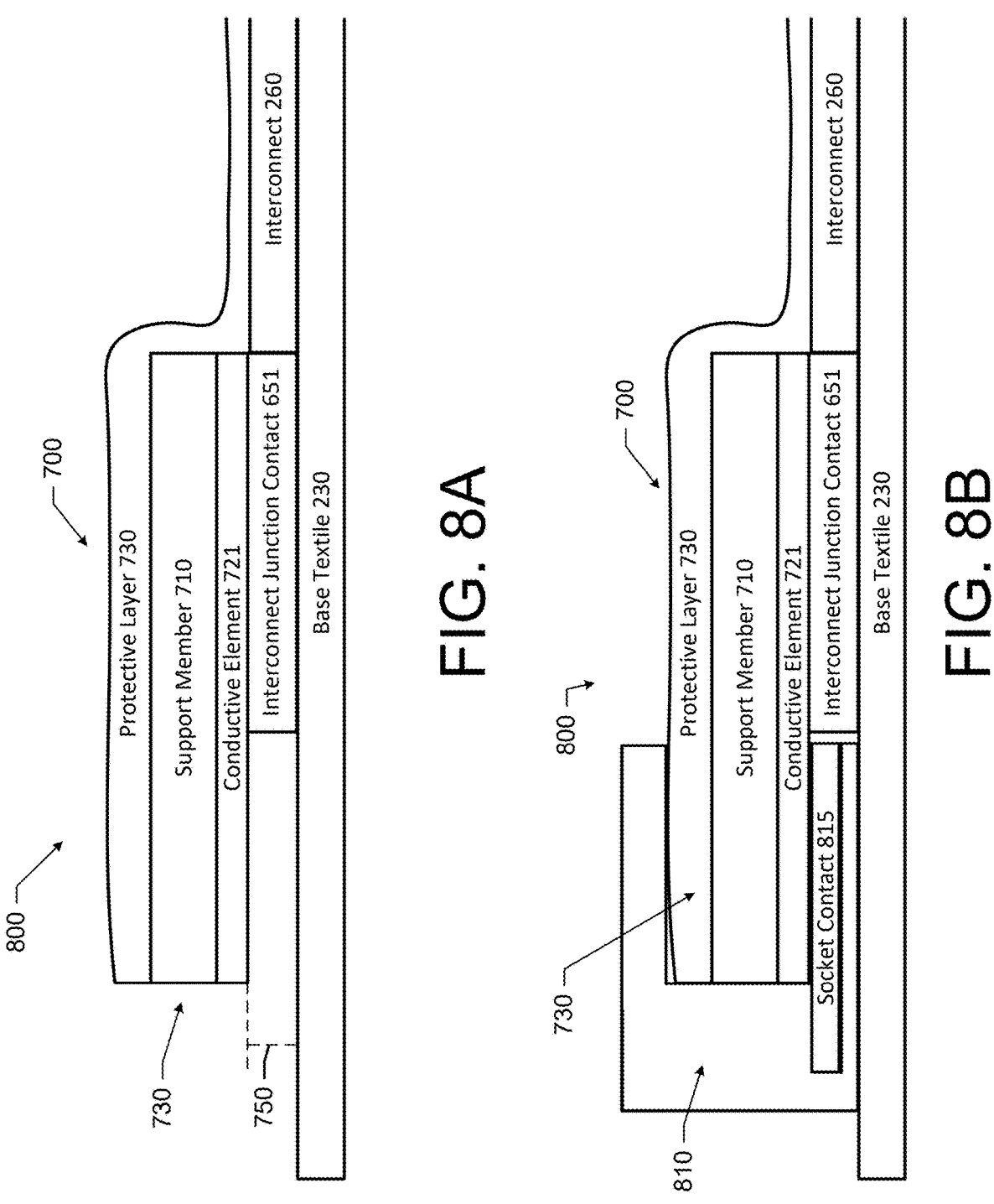
FIG. 8A illustrates cross-section view of a tab assembly according to some example embodiments.
FIG. 8B illustrates a cross-section view of a tab assembly engaged with a circuit board socket according to some example embodiments.

Now referring to FIG. 8A, a cross-section view of a tab arrangement 800 according to some example embodiments is provided. The tab arrangement 800 may comprise the tab assembly 700, with some additional components, coupled to an interconnect junction contact 651. In this regard, the base textile 230 may have the interconnect 260 affixed thereto, which may terminate at the interconnect junction contact 651. The tab assembly 700, comprising the support member 710 and the conductive element 721, may be affixed to the interconnect junction contact 651 via an adhesive, such as a conductive adhesive. More specifically, the pad 720 of the conductive element 721 may be adhered to the interconnect junction contact 651.

According to some example embodiments, a non-conductive adhesive may be used affix the conductive element 721 (and more specifically the pad 720) to the interconnect junction contact 651. For example, a non-conductive heat lamination adhesive may be used. Rather unexpectedly, non-conductive adhesives used in this application are possible because the conductive knit fibers of the material used to form the interconnect junction contact 651 (e.g., conductive textiles comprising synthetic elastane fibers with a conductive coating or synthetic elastane fibers woven with conductive fiber) may penetrate through the adhesive to make electrical contact (e.g., direct physical contact) with the conductive element 721 and form a mechanical coupling. As such, according to some example embodiments, a patterned conductive adhesive layer may be unnecessary to couple the interconnect junction contact 651 to the conductive element 721 to mechanically connect the components and form an electrical connection when a non-conductive adhesive is used.

The tab assembly 700 may be positioned to have a portion that overhangs the base textile 230 and, due to the thickness of the interconnect 160 and the interconnect junction contact 651, a gap 750 may be formed between the overhanging portion and the base textile 230. This overhanging portion may be referred to as the plug 730. Additionally, to protect the tab assembly 700 and the connection to the interconnect junction contact 651, the tab arrangement 800, and the muscle activity sensor, may include a protective layer 730. The protective layer 730 may be adhered over the tab assembly 700 and the interconnect 260. According to some example embodiments, the protective layer 730 may be disposed over each element of the muscle activity sensor (e.g., the electrode, the interconnect, and tab assembly). According to some example embodiments, the protective layer 730 may be formed of or comprise a thermoplastic polyurethane or other suitable polymer that has an elastic property. With the tab assembly 700 affixed to the interconnect junction contacts, the tab assembly 700 may be permitted to bend and deflect without separating from the interconnect junction contacts.

Referring now to FIG. 8B, a cross-section view of tab arrangement 800 engaged with a circuit board socket 810 is shown, according to some example embodiments. In this regard, the circuit board socket 810 may include a receiving cavity that receives the plug 730 such that a portion of the circuit board socket 810 slides into the gap 750 between the conductive element 721 and the base textile 230. The circuit board socket 810 may include one or more socket contacts 815 that electrically connects to a respective conductive element 721 of the tab assembly 700. As such, via the circuit board socket 810, the electrical signals initially detected by the electrodes of the muscle activity sensor may be provided to processing circuitry coupled to the circuit board socket 810 or otherwise in communication with circuit board socket 810 for signal analysis.

Some example embodiments will now be described in various optional configuration and combinations of elements that constitute some of the example embodiments described herein. In this regard, according to some example embodiments, a muscle activity electrode is provided. The muscle activity electrode may comprise a base textile, a sensor layer, and an interconnect. The base textile may be configured to apply a compression force against a dermal surface of a user. In this regard, the base textile may have a dermal side and an external side. The sensor layer may be coupled to the base textile and may comprise a conductive textile. The sensor layer may be configured to receive electrical signals associated with muscle activity of the user. The interconnect contact may be coupled to the base textile. A feedthrough element may be configured to form an electrical connection between the sensor layer and the interconnect contact to deliver the electrical signals from the sensor layer to the interconnect contact to be provided as an output signal. According to some example embodiments, a pressure layer may be disposed between the sensor layer and the base textile. The pressure layer may be configured to increase the compression force between the sensor layer and the dermal surface. Additionally or alternatively, the feedthrough element may be further configured to mechanically couple the sensor layer and the interconnect contact to the base textile. Additionally or alternatively, the conductive textile of the sensor layer comprises synthetic elastane fibers with a conductive coating or synthetic elastane fibers woven with conductive fibers. Additionally or alternatively, the conductive textile of the sensor layer may comprise PEDOT.PSS-coated polyester. Additionally or alternatively, the feedthrough element may comprise a conductive thread. Additionally or alternatively, the conductive textile of the sensor layer may be configured to absorb moisture to increase electrical conduction with the dermal surface.

According to some example embodiments, a muscle activity sensor is provided. The muscle activity sensor may comprise a base textile, an electrode, and an interconnect. The base textile may be configured to apply a compression force against a dermal surface of a user. In this regard, the base textile may have a dermal side and an external side. The electrode may be coupled to the base textile and may comprise a sensor layer comprising a conductive textile coupled to the dermal side of the base textile. The sensor layer may be configured to receive electrical signals associated with muscle activity of the user and the electrode may be configured to provide the electrical signals as an output signal. The interconnect may be coupled to the base textile over a distance from the electrode to an interconnect junction contact such that the interconnect moves with the base textile as the user moves. The interconnect may be configured to deliver the output signal from the electrode to the interconnect junction contact. Additionally, the interconnect may comprises synthetic elastane fibers with a conductive coating or synthetic elastane fibers woven with conductive fibers. Additionally or alternatively, the interconnect may comprise a portion that is formed in a serpentine pattern. Additionally or alternatively, the electrode may be a first electrode and the interconnect may be a first interconnect. The muscle activity sensor may further comprise a second electrode and a second interconnect. The first electrode and the second electrode may be positioned to receive the electrical signals associated with muscle activity of a common muscle. The first interconnect and the second interconnect may comprise respective portions that are formed in a nested serpentine pattern. Additionally or alternatively, the electrode may be a first electrode and the interconnect may be a first interconnect. The muscle activity sensor may further comprise a second electrode and a second interconnect. The first electrode and the second electrode may be positioned to receive the electrical signals associated with muscle activity of a common muscle. The first interconnect and the second interconnect may comprise respective portions that are formed as a twisted pair that transition through vias between the dermal side and the external side of the base textile. Additionally or alternatively, the muscle activity sensor may comprise a tab assembly configured to electrically connect the interconnect junction contact to a circuit board socket. The tab assembly may comprise a conductive element affixed to a support layer comprising a polyimide film. The conductive element may be electrically connected to the interconnect junction contact. The support layer and the conductive element may form an extension portion that extends over the base textile with a gap between the conductive element and the base textile such that the conductive element and the support layer form a plug configured to engage with the circuit board socket.

According to some example embodiments, another muscle activity sensor is provided. The muscle activity sensor may comprise a base textile, an electrode, an interconnect, and a tab assembly. The base textile may be configured to apply a compression force against a dermal surface of the user. The base textile may have a dermal side and an external side. The electrode may be coupled to the base textile and configured to receive electrical signals associated with muscle activity of the user and output the electrical signals as an output signal. The interconnect may be coupled to the base textile over a distance from the electrode to an interconnect junction contact such that the interconnect moves with the base textile as the user moves. The interconnect may be configured to deliver the output signal from the electrode to the interconnect junction contact. The tab assembly may be configured to electrically connect the junction to a circuit board socket. The tab assembly may comprise a conductive element affixed to a support layer, where the conductive element may be electrically connected to the interconnect junction contact. The support layer and the conductive element may form an extension portion that extends over the base textile with a gap between the conductive element and the base textile such that the conductive element and the support layer form a plug configured to engage with the circuit board socket. Additionally, the interconnect may comprise synthetic elastane fibers with a conductive coating or synthetic elastane fibers woven with conductive fibers. Additionally or alternatively, the interconnect may comprise a portion that is formed in a serpentine pattern. Additionally or alternatively, the electrode may be a first electrode and the interconnect may be a first interconnect. The muscle activity sensor may further comprise a second electrode and a second interconnect. The first electrode and the second electrode may be positioned to receive the electrical signals associated with muscle activity of a common muscle. The first interconnect and the second interconnect may comprise respective portions that are formed in a nested serpentine pattern. Additionally or alternatively, the first interconnect and the second interconnect may comprise respective portions that are formed as a twisted pair that transition through vias between the dermal side and the external side of the base textile. Additionally or alternatively, the support layer of the tab assembly may comprise a polyimide film.

The embodiments presented herein are provided as examples and therefore the disclosure is not to be limited to the specific embodiments disclosed. Modifications and other embodiments are intended to be included within the scope of the appended claims. Moreover, although the foregoing descriptions and the associated drawings describe example embodiments in the context of certain example combinations of elements and/or functions, different combinations of elements and/or functions may be used to form alternative embodiments. In this regard, for example, different combinations of elements and/or functions other than those explicitly described above are also contemplated. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments.

What is claimed is:

1. A muscle activity sensor comprising:
    a base textile configured to apply a compression force against a dermal surface of a user, the base textile having a dermal side and an external side;
    an electrode coupled to the base textile and comprising a sensor layer comprising a conductive textile coupled to the dermal side of the base textile, the sensor layer being configured to receive electrical signals associated with muscle activity of the user and the electrode being configured to provide the electrical signals as an output signal; and
    an interconnect coupled to the base textile over a distance from the electrode to an interconnect junction contact such that the interconnect moves with the base textile as the user moves, the interconnect being configured to deliver the output signal from the electrode to the interconnect junction contact,
    wherein the electrode is a first electrode and the interconnect is a first interconnect;
    wherein the muscle activity sensor further comprises a second electrode and a second interconnect,
    wherein the first electrode and the second electrode are positioned to receive the electrical signals associated with muscle activity of a common muscle, and
    wherein the first interconnect and the second interconnect comprise respective portions that are formed as a twisted pair that transition through vias between the dermal side and the external side of the base textile.

2. The muscle activity sensor of claim 1 further comprising a tab assembly configured to electrically connect the interconnect junction contact to a circuit board socket;
    wherein the tab assembly comprises a conductive element affixed to a support layer comprising a polyimide film, the conductive element being electrically connected to the interconnect junction contact, the support layer and the conductive element forming an extension portion that extends over the base textile with a gap between the conductive element and the base textile such that the conductive element and the support layer form a plug configured to engage with the circuit board socket.

3. A muscle activity sensor comprising:
    a base textile configured to apply a compression force against a dermal surface of a user, the base textile having a dermal side and an external side;
    an electrode coupled to the base textile and configured to receive electrical signals associated with muscle activity of the user and output the electrical signals as an output signal;
    an interconnect coupled to the base textile over a distance from the electrode to an interconnect junction contact such that the interconnect moves with the base textile as the user moves, the interconnect being configured to deliver the output signal from the electrode to the interconnect junction contact; and
    a tab assembly configured to electrically connect the interconnect junction to a circuit board socket,
    wherein the tab assembly comprises a conductive element affixed to a support layer, the conductive element being electrically connected to the interconnect junction contact, the support layer and the conductive element forming an extension portion that extends over the base textile with a gap between the conductive element and the base textile such that the conductive element and the support layer form a plug configured to engage with the circuit board socket,
    wherein the electrode is a first electrode and the interconnect is a first interconnect;
    wherein the muscle activity sensor further comprises a second electrode and a second interconnect,
    wherein the first electrode and the second electrode are positioned to receive the electrical signals associated with muscle activity of a common muscle, and
    wherein the first interconnect and the second interconnect comprise respective portions that are formed as a twisted pair that transition through vias between the dermal side and the external side of the base textile.

4. The muscle activity sensor of claim 1, further comprising a pressure layer disposed between the sensor layer and the base textile, the pressure layer being configured to increase the compression force between the sensor layer and the dermal surface.

5. The muscle activity sensor of claim 1, wherein the conductive textile of the sensor layer comprises synthetic elastane fibers with a conductive coating or synthetic elastane fibers woven with conductive fibers.

6. The muscle activity sensor of claim 1, wherein the conductive textile of the sensor layer comprises poly(3,4-ethylenedioxythiophene) polystyrene sulfonate (PEDOT: PSS)-coated polyester.

7. The muscle activity sensor of claim 1, wherein the conductive textile of the sensor layer is configured to absorb moisture to increase electrical conduction between the sensor layer and the dermal surface.

8. The muscle activity sensor of claim 3, wherein the conductive textile of the sensor layer is configured to absorb moisture to increase electrical conduction between the sensor layer and the dermal surface.

9. The muscle activity sensor of claim 8 wherein the support layer comprises a polyimide film.

10. The muscle activity sensor of claim 8, further comprising a pressure layer disposed between the sensor layer and the base textile, the pressure layer being configured to increase the compression force between the sensor layer and the dermal surface.

11. The muscle activity sensor of claim 8, wherein the conductive textile of the sensor layer comprises synthetic elastane fibers with a conductive coating or synthetic elastane fibers woven with conductive fibers.

12. The muscle activity sensor of claim 8, wherein the conductive textile of the sensor layer comprises poly(3,4-ethylenedioxythiophene) polystyrene sulfonate (PEDOT: PSS)-coated polyester.

* * * * *